United States Patent
Takahashi et al.

(10) Patent No.: US 10,302,779 B2
(45) Date of Patent: May 28, 2019

(54) RADIATION DETECTOR, RADIATION IMAGING DEVICE, COMPUTER TOMOGRAPHY DEVICE, AND RADIATION DETECTION METHOD

(71) Applicant: HITACHI, LTD., Tokyo (JP)

(72) Inventors: Isao Takahashi, Tokyo (JP); Kazuma Yokoi, Tokyo (JP); Eiji Moro, Tokyo (JP); Yuichiro Ueno, Tokyo (JP); Yasutaka Konno, Tokyo (JP); Fumito Watanabe, Tokyo (JP); Shinichi Kojima, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 232 days.

(21) Appl. No.: 15/518,575

(22) PCT Filed: Jun. 18, 2015

(86) PCT No.: PCT/JP2015/067584
§ 371 (c)(1),
(2) Date: Apr. 12, 2017

(87) PCT Pub. No.: WO2016/059830
PCT Pub. Date: Apr. 21, 2016

(65) Prior Publication Data
US 2017/0276808 A1     Sep. 28, 2017

(30) Foreign Application Priority Data
Oct. 16, 2014   (JP) .................................. 2014-211313

(51) Int. Cl.
*G01T 1/29*       (2006.01)
*H01L 31/115*     (2006.01)
(Continued)

(52) U.S. Cl.
CPC ............ *G01T 1/2985* (2013.01); *A61B 6/032* (2013.01); *A61B 6/4208* (2013.01); *G01T 1/161* (2013.01);
(Continued)

(58) Field of Classification Search
CPC ....... G01T 1/24; G01T 1/2928; G01T 1/2985; G01T 1/161; G01T 1/2018;
(Continued)

(56) References Cited

U.S. PATENT DOCUMENTS

2006/0056581 A1   3/2006   Hoffman et al.
2007/0140418 A1   6/2007   Hoffman et al.
(Continued)

FOREIGN PATENT DOCUMENTS

JP    2011-503535 A    1/2011
JP       5215722 B2    6/2013
WO   2009/060341 A2   5/2009

OTHER PUBLICATIONS

International Search Report of PCT/JP2015/067584 dated Jul. 28, 2015.

*Primary Examiner* — Don K Wong
(74) *Attorney, Agent, or Firm* — Mattingly & Malur, PC

(57) ABSTRACT

A flat pixel (20) is a single unit composing a radiation detector and is configured so as to be divided into at least four subpixels (21) such that even if a prescribed number of subpixels (21) are removed from each pixel (20) in order of largest effective area, the centroid (51) of the effective area of the entirety of the remaining subpixels (21) is positioned within a similar-shape region (30) having the same centroid (50) as the pixel (20) and having sides of lengths that are half those of the pixel (20).

12 Claims, 7 Drawing Sheets

(51) Int. Cl.
*G01T 1/161* (2006.01)
*G01T 1/17* (2006.01)
*G01T 1/20* (2006.01)
*H01L 27/146* (2006.01)
*A61B 6/03* (2006.01)
*A61B 6/00* (2006.01)

(52) U.S. Cl.
CPC .............. *G01T 1/17* (2013.01); *G01T 1/2018* (2013.01); *H01L 27/14658* (2013.01); *H01L 31/115* (2013.01)

(58) Field of Classification Search
CPC ......... H01L 27/14603; H01L 27/14609; H01L 31/1013; H01L 27/14601; H01L 2924/0002; H01L 31/115; H01L 2924/10
See application file for complete search history.

(56) References Cited

U.S. PATENT DOCUMENTS

| | | |
|---|---|---|
| 2007/0206721 A1 | 9/2007 | Tkaczyk et al. |
| 2007/0206722 A1 | 9/2007 | Hoffman et al. |
| 2007/0248209 A1 | 10/2007 | Hoffman et al. |
| 2008/0304618 A1 | 12/2008 | Hoffman et al. |
| 2009/0080601 A1* | 3/2009 | Tkaczyk ................ G01T 1/249 378/19 |
| 2010/0282972 A1 | 11/2010 | Carmi et al. |
| 2011/0155918 A1 | 6/2011 | Bouhnik et al. |
| 2013/0075620 A1 | 3/2013 | Nishino et al. |
| 2013/0193337 A1 | 8/2013 | Bouhnik et al. |

\* cited by examiner

[Fig. 1]
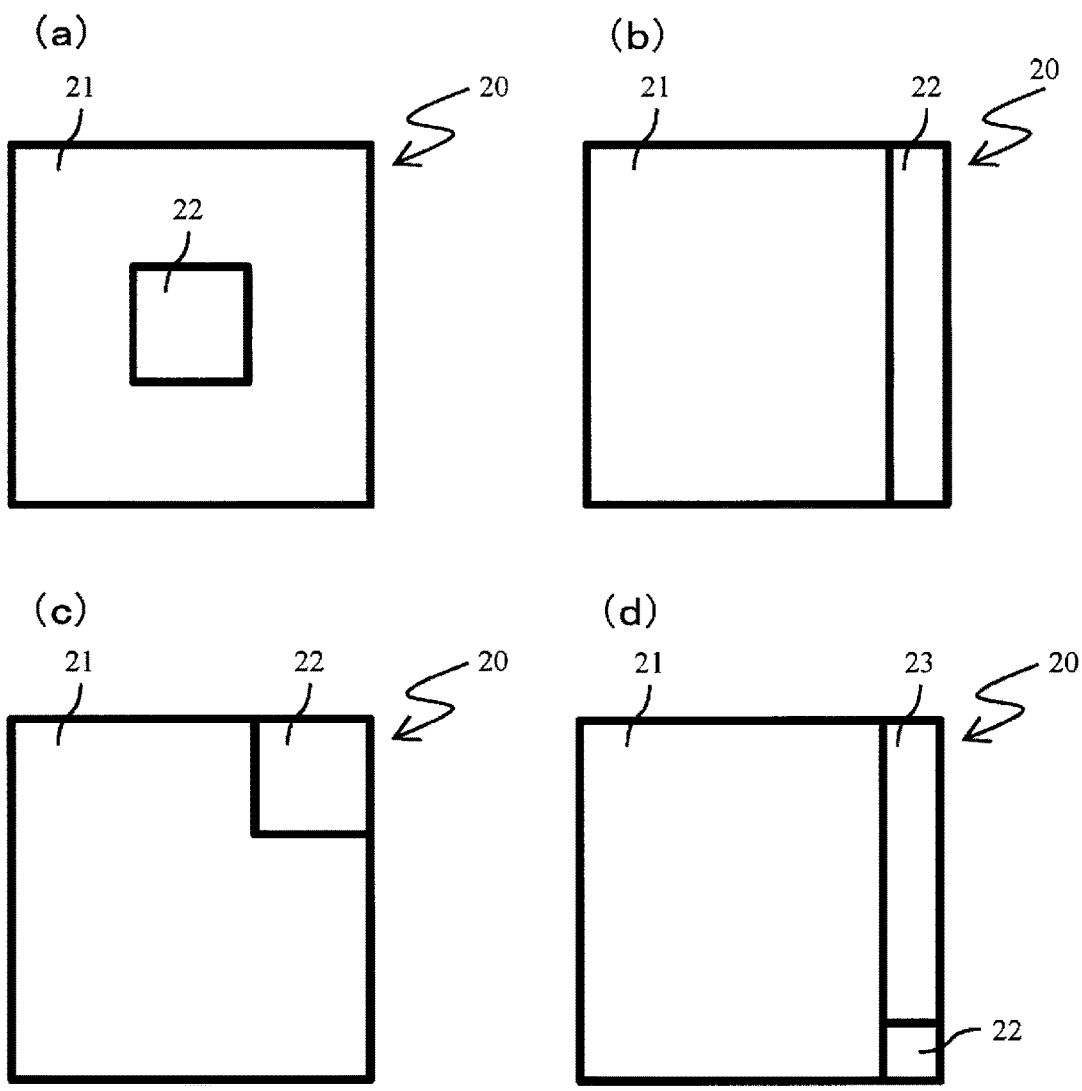

[Fig. 2]
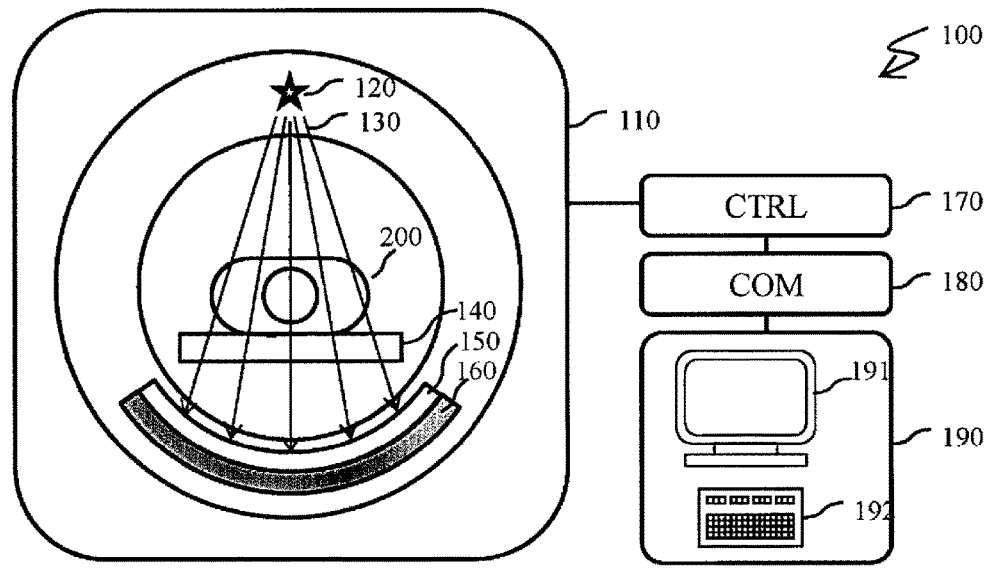
[Fig. 3]
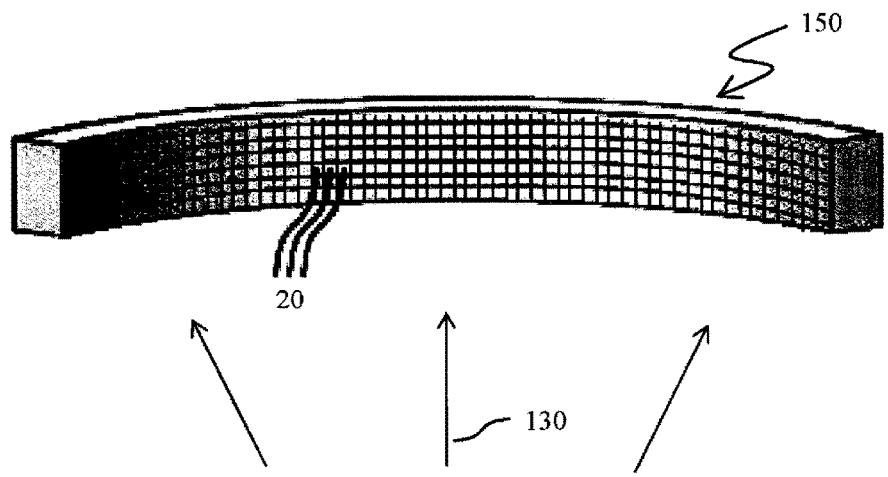

[Fig. 4]
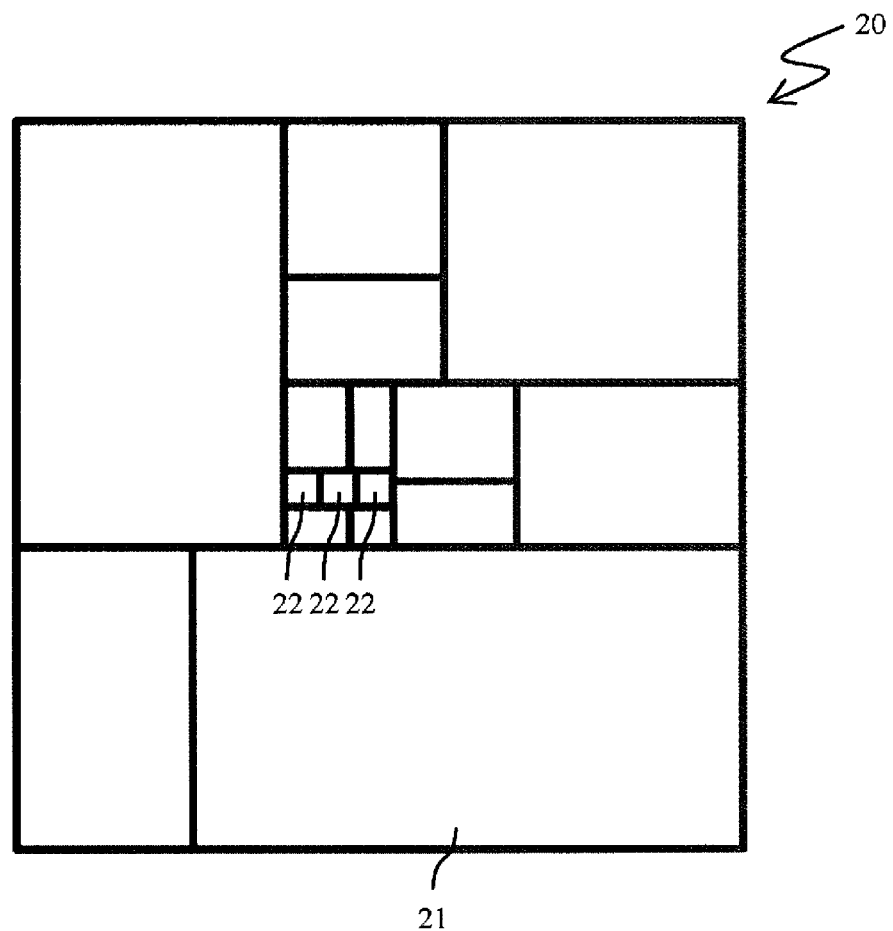

[Fig. 5]
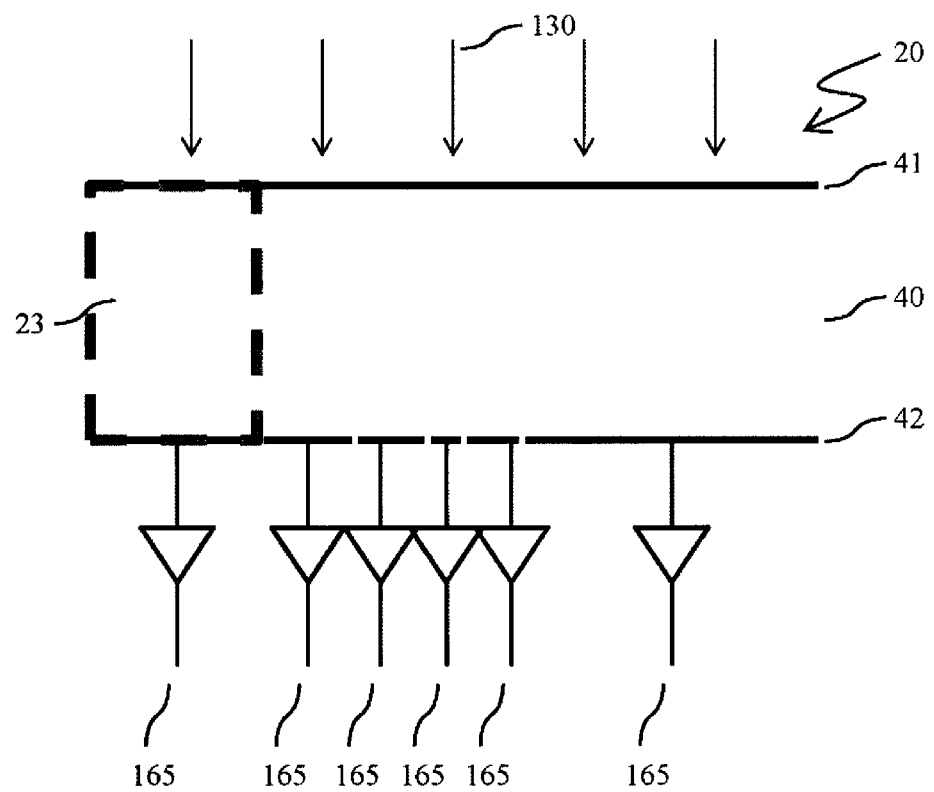

[Fig. 6]
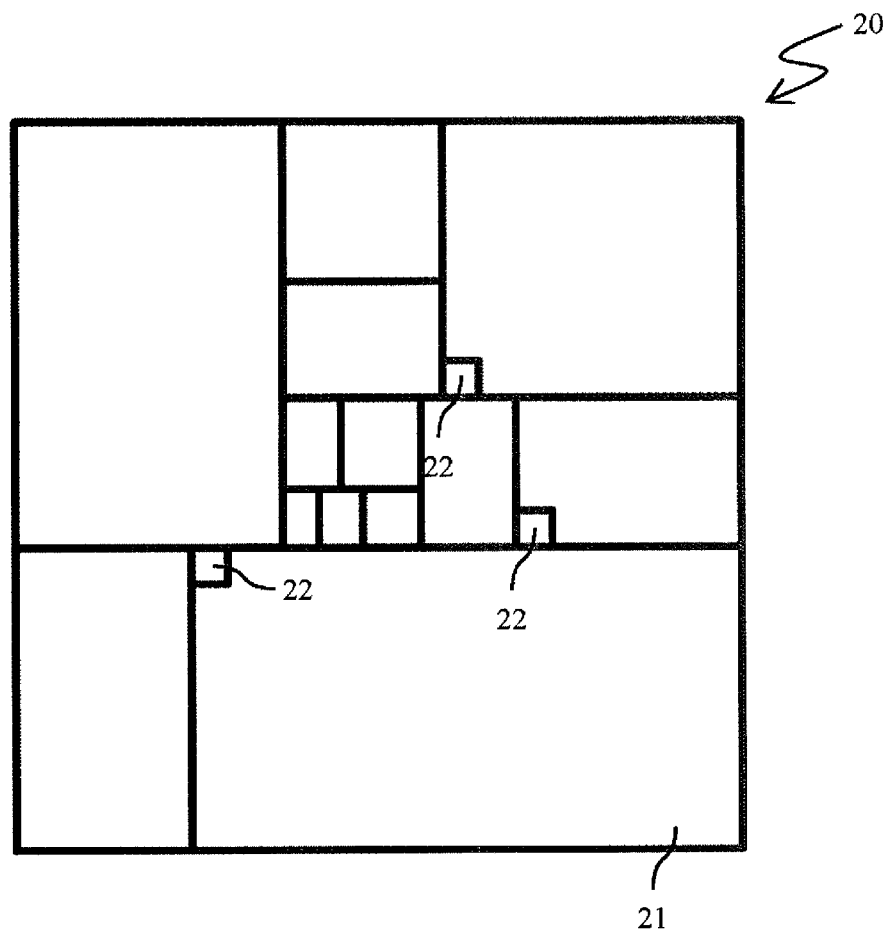

[Fig. 7]
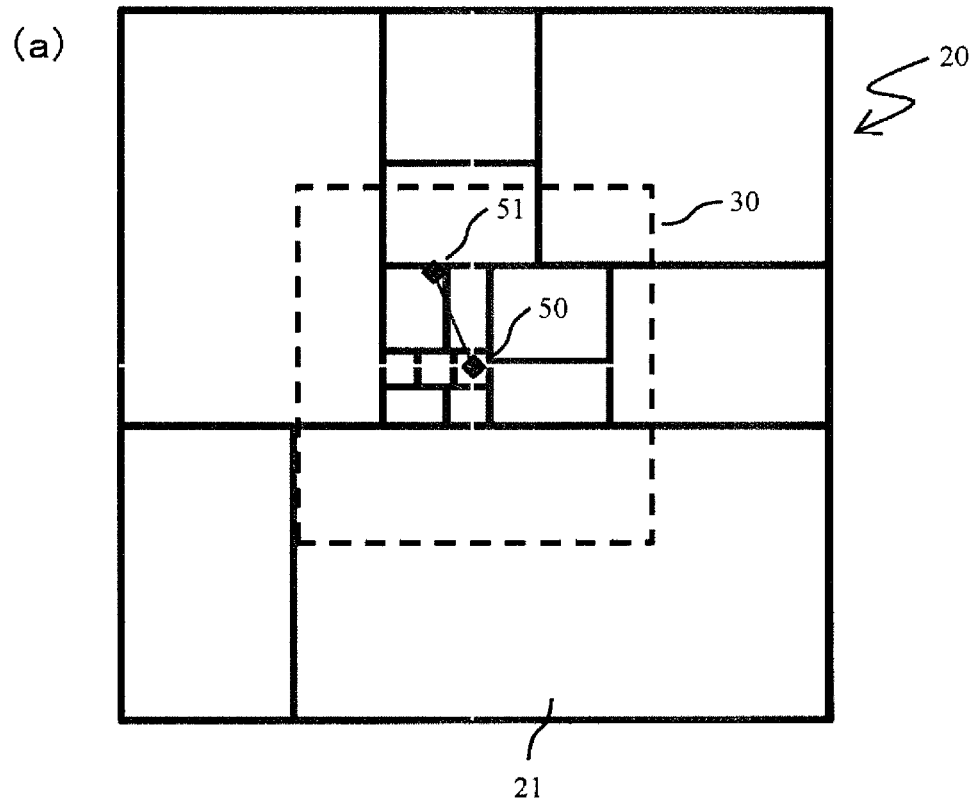
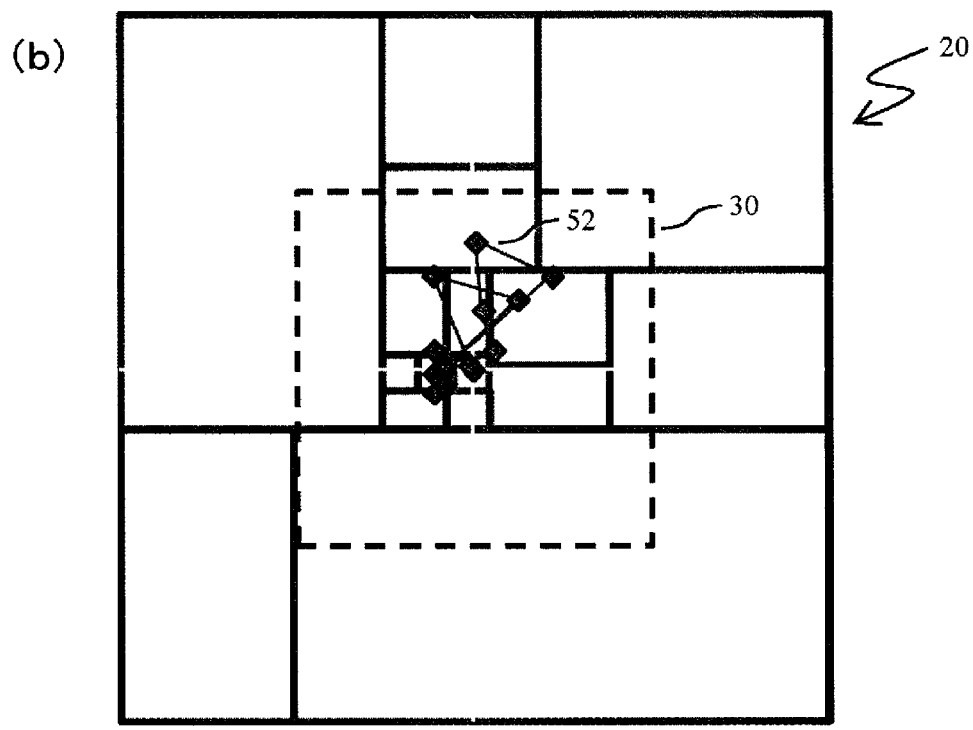

[Fig. 8]
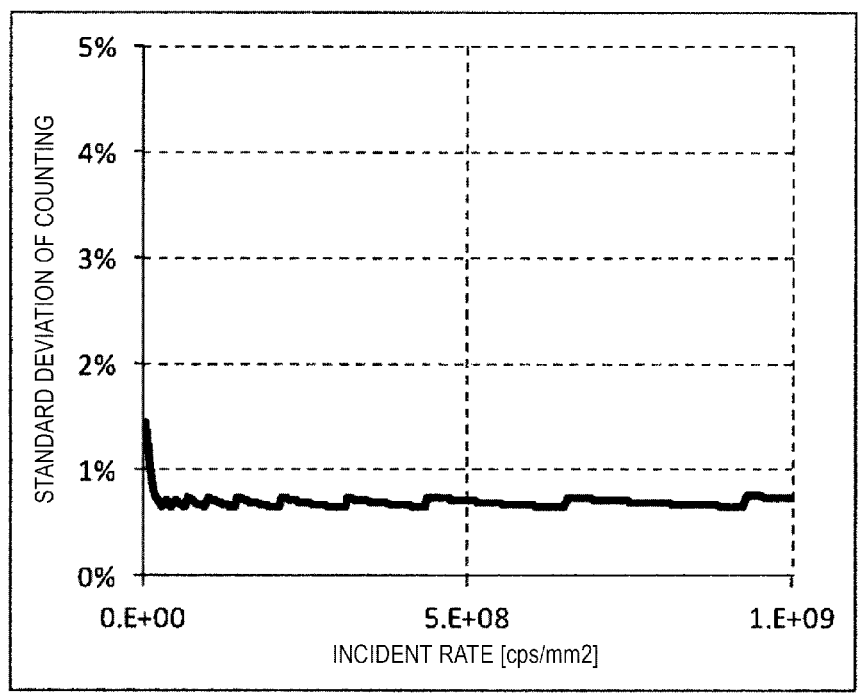

RADIATION DETECTOR, RADIATION IMAGING DEVICE, COMPUTER TOMOGRAPHY DEVICE, AND RADIATION DETECTION METHOD

TECHNICAL FIELD

The present invention relates to a radiation detector, a radiation imaging device, a computer tomography device, and a radiation detection method.

BACKGROUND ART

In recent years, there are active movements for realizing higher precise devices by operating radiation detectors in a pulse mode, that is, analyzing and detecting radiation rays one by one. In relation to the movements, PTL 1 and PTL 2 disclose detectors in which subpixels with different sizes are provided.

CITATION LIST

Patent Literature

PTL 1: JP-T-2011-503535
PTL 2: Japanese Patent No. 5215722

SUMMARY OF INVENTION

Technical Problem

In the pulse mode, there is a problem that a detector is saturated in a case in which an incident rate of a radiation ray is high. To deal with this problem, the foregoing documents disclose small square subpixels provided in the middles of square pixels or small rectangular subpixels provided in corners of square pixels. When the number of subpixels is increased, detectors are miniaturized or the density of a processing circuit increases, and therefore a circumstance in which a difficulty in mounting or cost is involved is considered or a case in which the number of subpixels is mainly 2 or 3 even in the foregoing example is examined.

In regard to the present situation, the inventors have reached the following problems. In order not to saturate a detector even in a case in which an incident rate is high, it is necessary to sufficiently reduce a smallest subpixel. However, in order to suppress deterioration in measurement precision, it is necessary not to considerably increase an area difference between pixels. On the other hand, in order to take measurement with high precision even in a case in which the incident rate is low, a pixel may not have an excessively small size. When a small subpixel is located in a corner of a pixel, an error may easily occur or an influence of the shadow of a collimator may increase.

The invention is devised in view of the foregoing problem and an object of the invention is to provide a radiation detector capable of performing radiation measurement with high precision in a broad incident-rate region.

Solution to Problem

To achieve the foregoing object, a radiation detector of the invention includes a plurality of flat pixels configured to detect a radiation ray. The pixel is divided into four or more subpixels of which at least two subpixels have different effective areas. The pixel is divided into the subpixels so that even when an arbitrary number of subpixels less than the number of subpixels obtained by dividing the pixel is removed from the pixel in order of larger effective areas, a centroid of the effective area of the entirety of the remaining subpixels is positioned within a similar-shape region having the same centroid as the pixel and having sides of lengths that are half those of the pixel.

Advantageous Effects of Invention

The invention can provide a radiation detector capable of performing radiation measurement with high precision in a broad incident-rate region and provide a CT using the radiation detector so that mounting or cost is advantageous.

BRIEF DESCRIPTION OF DRAWINGS

FIG. 1 is a schematic diagram illustrating a form of subpixel division of a radiation detector according to an example of a related art.

FIG. 2 is a schematic diagram illustrating a CT using a radiation detector according to an embodiment of the invention.

FIG. 3 is a schematic diagram illustrating the plurality of disposed radiation detectors according to the embodiment of the invention.

FIG. 4 is a schematic diagram (front view) illustrating the radiation detector according to the embodiment of the invention.

FIG. 5 is a schematic diagram (sectional view) illustrating the radiation detector according to the embodiment of the invention.

FIG. 6 is a schematic diagram (front view) illustrating the radiation detector according to the embodiment of the invention.

FIG. 7 is a schematic diagram illustrating centroid positions of subpixels in the radiation detector according to the embodiment of the invention.

FIG. 8 is a schematic diagram illustrating a standard deviation of counting from an incident rate in the radiation detector according to the embodiment of the invention.

DESCRIPTION OF EMBODIMENTS

The technical meaning of the invention and the like will be described before an embodiment of the invention is described. In the present application, an example in which a medical diagnosis device using an X ray is a device to which the radiation detector is applied will be mainly described.

(Description of Technical Meaning and the Like of the Invention)

In general, in a medical diagnosis device using an X ray, for example, a computer tomography device (CT), an object is irradiated with the X ray generated from an X ray source and the X ray is detected by a radiation detector. Thus, the form of an object inside a body is imaged to be provided for diagnosis by obtaining information regarding the degree of attenuation of the X ray by the object.

In a general whole-body CT used currently, X ray is generated from an X-ray tube to which a high voltage is applied and scintillator detects the X-ray transmitted through an object. When the X ray scattered in the object is detected, an undesirable signal is generated. Therefore, a collimator is generally disposed in front of the scintillator when viewed from the X-ray tube side to block the scattered X ray. The X ray detected by the scintillator is converted into fluorescence. The fluorescence is read by a photodevices such as photodiodes and is output as an electric signal. The detector system is operated in a so-called current mode (or an integrating mode). That is, a total amount of the electric signal generated for a given time span, for example, 1 millisecond, is a measurement value and X-ray photons are not analyzed one by one. Accordingly, for example, the same measurement result is obtained between a case in which one X-ray photon with energy of 100 keV is detected and a case in which two X-ray photons with energy of 50 keV are detected.

In recent years, there is an active movement for realizing a higher precise diagnosis device by operating a detector system in a pulse mode rather than a current mode, that is, analyzing and detecting X-ray photons one by one. By analyzing and detecting the X-ray photons, it is possible to obtain energy information of X-ray photons which may not be obtained in an existing CT. Thus, it is expected that material decomposition or low radiation dose which may not be realized in an existing CT can be realized.

In a case in which a detector of a CT is operated in a pulse mode, a major problem is that an incident rate of X-ray photons is considerably high. In a general whole-body CT, X-ray photons of an order of a maximum of $10^9$ per second per square millimeter of the detector ($10^9$ cps/mm$^2$) are detected in some cases. The size of a pixel in a general detector in the CT is an order of 1 mm in square. For example, when 50 nanoseconds are necessary for a detector system to process a signal of one X-ray photon, several tens of signals of other X-ray photons may be generated while signal processing is performed on a certain X-ray photon, or signals of two or more X-ray photons may be misidentified as a signal of one X-ray photon to be subjected to signal processing (so-called pile-up). This state is a state in which a detector is saturated. When the detector is saturated, X-ray photons may not correctly be counted and energy information may not correctly be obtained.

To treat with the problem of "high incident rate correspondence of detector", there are several techniques.

One technique is a technique for dividing one pixel into a plurality of smaller subpixels and connecting an independent signal processing circuit to each subpixel. For example, when a pixel with 1 mm in square is divided into 16 subpixels with 0.25 mm in square, count rate characteristics can be expected to be improved simply 16 times. When the number of divisions is increased and the count rate characteristics per area are accordingly improved, the detectors are miniaturized and the density of signal processing circuits also increases. Therefore, the excessive division causes a difficulty in mounting or cost.

As a technique corresponding to a high incident rate while suppressing the number of divisions, a technique for providing subpixels with different sizes is disclosed in PTL 1 or PTL 2. In a region in which an incident rate is low, X-ray photons are counted with all the subpixels. In a region in which an incident rate is high, subpixels with broad areas may be saturated. Since subpixels with narrow areas can continuously be counted, X-ray counting is possible even at a higher incident rate.

PTL 1 and PTL 2 disclose techniques illustrated in FIGS. 1(a) to 1(d) as forms of division into subpixels with different areas. FIG. 1(a) illustrates a division method into subpixels disclosed in FIG. 5A of PTL 1 and FIG. 19 of PTL 2. PTL 1 discloses two subpixels of which centroids may be identical. This case tells that symmetry is good, which is advantageous to rebinning. PTL 2 tells that crosstalk between subpixels is small when small subpixels are disposed in middle. FIG. 1(b) illustrates a division method into subpixels disclosed in FIG. 5B of PTL 1. PTL 1 discloses that centroids of two subpixels may be different. This case tells that manufacturing is easier than in FIG. 1(a). FIG. 1(c) illustrates a division method into subpixels disclosed in FIG. 18 of PTL 2. FIG. 1(d) illustrates a division method into subpixels disclosed in FIG. 3 of PTL 1 and illustrates a form of division into three subpixels.

However, in a case in which subpixel division illustrated in FIGS. 1(b), 1(c), and 1(d) is performed, smallest subpixels 22 are located in the vicinity of the outer circumferences of pixels. When an incident rate is increased, saturation occurs from a subpixel with a large area and counting may not be performed. Thus, in a region in which the incident rate is highest, only the smallest subpixel 22 counts X-ray photons in a certain situation. That is, only X-ray photons arriving at the vicinity of the outer circumference of the pixel are detected. However, in this case, the following problems occur. One problem is a sampling problem. In a CT, data is collected through rotation around an object. There is known a technique for realizing fineness of effective sampling intervals by disposing a detector so that the detector is deviated by a quarter pixel from a rotation center between when the detectors are located at a position of 0 degrees and when the detectors are located at a position of 180 degrees (a so-called quarter offset method). However, in sub-pixelization methods of FIGS. 1(b), 1(c), and 1(d), only signals of the outer circumference of a pixel in a region in which an incident rate is highest are detected, and therefore an error occurs in sampling and image quality may deteriorate. There is known a technique for realizing fineness of effective sampling intervals by acquiring data while moving a focus of an X-ray tube slightly (a so-called flying focus method). Even in this case, image quality may deteriorate similarly. One more problem is an influence of the shade of a collimator. The collimator is installed to surround the entire circumference of one pixel. However, when manufacturing precision of the collimator is not ideal, the shadow of the collimator is in the subpixel 22. Since the subpixel 22 with a small area is located in the circumference which is easily affected by the shadow, it is considered that there is a considerable influence on the counting of the X-ray photons. Even in this case, the image quality may deteriorate.

In practice, a problem occurs when a pixel is divided into two or three subpixels. To maintain image quality satisfied for diagnosis supply, it is necessary to detect a sufficient number of X-ray photons. Therefore, to perform counting with high precision even in a region in which an incident rate is low, a pixel 20 may not have an excessively small size. In contrast, to correspond to a sufficiently high incident rate without saturating the detector, it is necessary for the smallest subpixel 22 to take a sufficiently small area, for example, in FIG. 1(a). Then, an area ratio to a largest subpixel 21 increases, and thus the number of counted X-ray photons considerably differs for each subpixel. In this case, at a low incident rate, X-ray photons are counted in the subpixels 21 and 22. When the incident rate is gradually increased and the largest subpixel 21 is saturated, the area of the detector contributing to the counting of the X-ray photons sharply decreases, the precision of the counting sharply deteriorates, and a statistical error sharply increases discontinuously, thereby having an adverse influence on the image quality. That is, to suppress the adverse influence on the image quality, it is necessary for one pixel to have a sufficient size, it is necessary for the smallest subpixel to be sufficiently small, and it is necessary for an area difference in each subpixel not to be excessively large. To realize this necessity, the number of subpixels has to be set to a large number to some extent. Thus, the number of subpixels is at least 4 or more.

Hereinafter, an embodiment of the invention will be described with reference to the drawings.

(CT)

In an embodiment, a schematic diagram of a CT 100 using a plurality of radiation detectors 150 according to the invention is illustrated as an embodiment in FIG. 2. An object 200 is lying on a bed 140 and is disposed near the center of the device in an opening near the center of a gantry 110. It is quite suitable to use an X-ray tube as an X-ray source 120. X-ray photons 130 are radiated from the X-ray tube, some of the X-ray photons are absorbed according to a body substance distribution by the object 200, and some of the X-ray photons are transmitted through the object 200 to be detected by the plurality of radiation detectors 150. The detected X-ray photons are counted in a pulse mode by a signal processing circuit 160. The counting mentioned here includes counting the detected X-ray photons and acquiring energy information.

In the CT, it is general to acquire data from in all the directions. Therefore, the X-ray source 120 and the plurality of radiation detectors 150 acquire data while being rotated around the object 200. A rotation speed is typically 1 to 4 rotations per second. A time in which the data for acquiring projection data in a certain direction (one view) is accumulated is typically an order of 0.1 to 1 millisecond. A scheme in which the X-ray source 120 and the plurality of radiation detectors 150 covering the entire object 200 are rotated around the object 200 as in the embodiment is referred to as a 3rd-generation CT, but the invention can also be applied to other CTs.

The plurality of radiation detectors 150 are disposed so that the radiation detectors 150 are deviated in a pitch by a quarter of the pixel from a rotation center between when the detectors are located at a position of 0 degrees and when the detectors are located at a position of 180 degrees (so-called quarter offset).

The rotation operation of the X-ray source 120, the emission of the X-ray photons 130, the movement of the bed 140, and other operations are controlled in accordance with signals from a control device 170 of the CT. The control device 170 also serves as processing a signal from the signal processing circuit 160 and transmitting the signal to a computer 180.

The computer 180 performs reconstruction of tomographic images based on an obtained projection data group in the directions. The tomographic images are finally output from an output device 191 to be supplied for diagnosis. In addition, parameters necessary to collect data, for example, a tube current or the value of a voltage applied from a high-voltage power supply (not illustrated) to the X-ray tube, a speed of the rotation operation of the X-ray source 120, are input from an input device 192 and the forms can be confirmed with the output device 191.

(Configuration of Radiation Detector)

The form of the plurality of radiation detectors 150 is illustrated in FIG. 3. The pixels 20, each of which is a single unit of the radiation detector, are disposed in a 2-dimensional shape. The number of pixels is, for example, 892 in the longitudinal direction and is 64 in the transverse direction. In FIG. 3, the pixels 20 are depicted to be approximately disposed in a curve shape. However, many pixel surfaces are generally flat surfaces without curvature. Therefore, the detectors can also be disposed in a polygonal shape. The X-ray photons 130 transmitted through the object 200 are incident on the pixels 20 to be counted. To remove the X-ray photons scattered in the object 200, collimators (not illustrated) are disposed in front of the pixels 20. The collimators may be 2-dimensional square hole collimators which have pitches and shapes identical to the pixels 20 or may be 1-dimensional slit collimators.

FIG. 4 is a conceptual diagram illustrating one pixel 20 when viewed in a direction in which the X-ray photons are incident. The pixel 20 has a size of 1 mm in square and is divided into 16 subpixels. As a material of the detector, a material in which a photodevice is optically coupled in a scintillator (indirect radiation detection material) can also be used. However, it is suitable to use a direct radiation detection material, such as cadmium telluride, cadmium zinc telluride, thallium bromide, or mercury iodide, for which minute processing is easy and an electric signal is directly readable.

The 16 subpixels have various effective areas. The subpixels with the large effective areas are disposed on the outer circumference side of the pixel 20 and the middle and small subpixels are disposed to fill the gaps of the subpixels with the large effective areas. Roughly, the large subpixels are disposed in the outer circumference and the smaller subpixels are disposed in the inner circumference. "Roughly" means that this disposition is not precise; it is also intended that the subpixels fill inside the pixel 20 without large gaps.

FIG. 5 is a sectional view illustrating the pixel 20 when a direct radiation detection material 40 is used as a material of the detector. An appropriate thickness of the direct radiation detection material 40 is about 0.5 mm to 3 mm. A common electrode 41 covering the entire pixel is formed on the upper surface of the direct radiation detection material which is an incident surface of the X-ray photons 130. A high-voltage power supply (not illustrated) applies, for example, a voltage of −600 V to the common electrode 41. On the other hand, a subpixel electrode 42 is formed for each subpixel on the lower surface, an individual channel 165 of the signal processing circuit is connected to each subpixel electrode 42 to read a signal, and acquiring energy information and counting X-ray photons are performed. Preferably, the X-ray photons are not attenuated in the common electrode 41 and the subpixel electrodes 42. It is known that these electrodes are sufficiently thinner than the direct radiation detection material 40 and can be set to have a thickness equal to or less than 1 micrometer.

As indicated by a dotted line in FIG. 5, a region corresponding to the subpixel electrode 42 forms each subpixel 23 in the direct radiation detection material 40. In this way, in a case in which the direct radiation detection material is used as the material of the detector, the boundaries of the subpixels depicted in FIG. 4 are not seen physically in some cases in a view from the upper surface of the pixel 20. However, radiation detectors are divided in the subpixels.

(Operation of Pixels According to Incident Rate)

Since all the subpixels are not saturated in a region in which an incident rate of the X-ray photons is low, incident X-ray photons can be correctly counted, thereby contributing to acquisition of data. When the incident rate is increased, the largest subpixel 21 is first saturated, and thus the X-ray photons may not correctly be counted. In this case, since the subpixels are not saturated except for the largest subpixel 21, the X-ray photons can correctly be counted using the count data. When the incident rate is further increased, the second largest subpixel is saturated. Therefore, the X-ray photons are counted using count data of the 14 subpixels except for the second largest subpixel. In this way, only the subpixels which are not saturated are used according to the incident rate and the X-ray photons are counted using only the smallest subpixel 22 which is not saturated in a region in which the incident rate is highest. At the time of a process of reconstructing a tomographic image, a process of correcting the size of the pixel is performed by considering a subpixel which contributes to the acquisition of the data.

When the actual count data is treated, an output of the pixel can be obtained by taking all the count data from the 16 subpixels in the computer 180 and removing the data of the saturated subpixel and collecting only the data of the unsaturated subpixels. In general, when the detector is saturated, energy information considerably deteriorates due to pile-up. Thus, by viewing the energy information, it is possible to determine which subpixel is saturated. As another method, the signal processing circuit 160 includes a mechanism that detects saturation so that data can be prevented in real time from being output from the saturated subpixel. In this case, since the amount of data transmitted to the computer 180 is narrowed, a burden on data transmission is relieved. As still another method, data of the saturated subpixel can be prevented from being output by predicting a subpixel which is saturated in a subsequently acquired view referring to one piece of count data of a previously obtained view as one reference. As still another method, data can be suppressed from being output from the saturated subpixel by predicting an incident rate of each pixel in each view on the basis of certain data of positioning scan performed before tomography is performed, that is, transmission data simply acquired without rotating the plurality of radiation detectors 150 around the object 200. As still another method, data can be prevented from being output from the saturated subpixel by predicting an incident rate of each pixel in each view on the basis of the height and weight of the object 200 and other parameters input from the input device 192.

(Division of Pixel into Subpixels)

In FIG. 4, the smallest subpixels 22 set to have 0.05 mm in square. By setting the sizes of the subpixels to be finer, it is possible to correspond to higher incident rates. However, in order for the radiation detector to perform a desirable operation, it is necessary to maintain an outer circumference-to-area ratio equal to or less than a given value because of the following reasons. The subpixels may not be set as small as possible. When the detectors detect the X-ray photons, primary electrons with high energy are generated inside the pixel 20 and secondary carriers are generated by ionizing the circumference while moving the primary electrons. Movement distances of the primary electrons are finite and can be escaped to nearby subpixels. Certain characteristic X-rays generated along with the primary electrons can also be escaped to nearby subpixels. Due to the facts, a so-called crosstalk effect may be considerable and the precision of the counting may deteriorate. This is a reason for necessarily maintaining the outer circumference-to-area ratio equal to or less than the given value. In a case in which an effective area of the subpixel is 0.05 mm in square, a count rate of the subpixel is obtained by multiplying $2.5 \times 10^6$ cps by detection efficiency (for example, 99%) of the detector even when the incident rate of the X-ray photons is $10^9$ cps/mm$^2$. Thus, counting can be performed without saturation in a signal processing circuit in which a response time is 50 nanoseconds.

When the entire pixel 20 is filled with subpixels with 0.05 mm in square, 400 divisions are necessary. Thus, a considerably high density of the signal processing circuit is required, a difficult in mounting and cost occurs. However, in the radiation detectors according to the embodiment, the sizes of the subpixels are variable and the subpixels are effectively disposed. Therefore, it is possible to correspond to a high incident rate while the number of divisions of the subpixels is suppressed to 16.

In FIG. 4, three smallest subpixels 22 with 0.05 mm in square are formed. The other 13 subpixels have mutually different effective areas and the pixel 20 is disposed to be entirely filled with the subpixels. As a division method for subpixels, disposition illustrated in FIG. 6 can also be considered. That is, a plurality of smallest subpixels 22 are formed at positions distant from each other. By doing so, the smallest subpixels 22 operate without being saturated even in regions in which the incident rate is highest. Therefore, it is possible to count the X-ray photons at distant positions inside the pixel and detect irregularity of transmission data inside the pixel. Further, although not introduced in the embodiment, it is meaningful that a plurality of subpixels with the same effective area rather than the smallest area are formed. For example, when subpixels with the same size are disposed at point-symmetric positions distant from each other centering on the centroid of the pixel 21, a precision improvement effect can be obtained.

By using small subpixels irrespective of the incident rate of the X-ray photons, it is possible to generate a diagnostic image in which a high frequency component is emphasized in regard to transmission data of the object 200.

As described above, when the outer circumference-to-area ratio of the subpixels is small, an undesirable operation occurs due to a crosstalk effect. For a figure with a certain area, a form which has a minimum outer circumference-to-area is a circle, but it is not possible to entirely fill the pixel with circular subpixels. Accordingly, the shapes of the subpixels are preferably squares or rectangles with an aspect ratio close to 1 and the subpixels preferably have solid shapes from the same viewpoint. Here, the solid shape means a shape which does not have a hollow portion such as a doughnut shape or a concave portion. Further, in FIG. 4, all the 16 subpixels have square or rectangular solid shapes and aspect ratios are set to be equal to or greater than 0.5 and equal to or less than 2.

(Centroid of Subpixel)

In each embodiment of the invention, by using only count data of the unsaturated subpixels, the areas contributing to acquisition of the data can be changed inside the pixel according to the incident rate. In a region in which the incident rate is low, all the subpixels are not saturated and the X-ray photons are correctly counted. Thus, the entire pixel contributes to the acquisition of the data. Basically, the centroid of the unsaturated subpixels is identical to a centroid 50 of the pixel, as illustrated in FIG. 7(*a*). When the incident rate is increased, the largest subpixel 21 is saturated and thus does not contribute to the acquisition of the data. In this case, the bottom right region of the pixel does not function in FIG. 7(*a*). Thus, the centroid 51 of the subpixels contributing to the acquisition of the data moves from the centroid 50 of the pixel to a top left side.

When the incident rate is increased and the number of saturated subpixels gradually increases, a movement trajectory 52 of the centroid of the subpixels contributing to the acquisition of the data is formed, as illustrated in FIG. 7(*b*). That is, in any situation, the centroid of the subpixels contributing to the acquisition of the data without being saturated remains within a region 30 in the vicinity of the center of the pixel 20. This is because the outer circumference of the pixel 20 is occupied by 6 larger subpixels and 10 smaller subpixels do not share sides with the pixel 20. Since the centroid of the subpixels contributing to the acquisition of the data is in the vicinity of the center of the pixel, a more representative value inside the pixel can be acquired as transmission data of the X-ray photons than when the centroid of the subpixels is near the outer circumference. Further, a desirable effect is also obtained from the viewpoint of a spatial resolution and artifact reduction.

The centroid of the subpixels contributing to the acquisition of the data is preferably closer to the centroid of the pixel. In consideration that the effective sampling density is doubled according to the quarter offset method, it is desirable that the centroid of the subpixels contributing to the acquisition of the data remains inside the region, which has the identical centroid of the pixel and has the similar shape with the size (length of each side) of half of the pixel. The position of the centroid of the subpixels contributing to the acquisition of the data is known. Therefore, in consideration of this fact, rebinning, a correction process, and the like in the process of reconstructing a tomographic image are performed. In the division of the subpixels, the subpixels are divided so that sampling in which a restriction is imposed on the reconstruction process due to a difference in the position of the centroid of the subpixels is not performed.

Since the centroid of the subpixels contributing to the acquisition of the data is in the vicinity of the center of the pixel, it is possible to obtain the effect that the subpixels rarely become the shadow of the collimators and an adverse influence on image quality rarely occurs.

(Effective Areas of Subpixels)

When the subpixels divided as N subpixels are arranged in a smaller order and effective areas are $a_1, a_2, \ldots, a_N$, set values of the effective areas will be described. When k smallest subpixels are formed, $a_1=a_2=\ldots=a_k<a_{k+1}<\ldots<a_N$. Here, as described above, three kinds of sizes of the subpixels are not sufficient, and thus $N \geq 4$ and $1 \leq k \leq N-3$ are set. The embodiment corresponds to a case in which N=16 and k=3.

A statistical error is given as a representative factor for deciding precision of the counting of the X-ray photons. According to the Poisson statistics, a statistical error of measurement in which 100 photons are counted is 10% obtained by dividing 10 which is a square root of 100 by 100. Incidentally, in the embodiment, only the subpixels which are not saturated contribute to acquisition of data in a region in which an incident rate of the X-ray photons is high. Accordingly, due to the saturation of a certain subpixel, a total area of the subpixels contributing to the acquisition of the data discontinuously decreases and the statistical error discontinuously increases. From the viewpoint of image quality, the division of the subpixels in which the statistical error does not discontinuously change due to the incident rate can be said to be desirable.

To realize the preferable division of the subpixels, the statistical error in the entire pixel, moreover, the counting number or a count rate, may be same between a situation in which an i+1-th small subpixel is saturated at a certain incident rate and only i subpixels contribute to the acquisition of the data and a situation in which the incident rate is increased, an i-th small subpixel is saturated and only i−1 subpixels contribute to the acquisition of the data. Here, i>k+1 is satisfied.

To formulate this situation, it is assumed that C is a count rate at which the signal processing circuit to which the subpixels are connected is saturated and $S_i$ is an incident rate per area in which an i-th small subpixel is saturated. At this time, $S_i = C/a_i$ is satisfied. When the condition (the count rate is the same) of the previous paragraph is expressed as an equation, Equation (1) is obtained.

$$S_{i+1} \times \sum_{j=1}^{i} a_j = S_i \times \sum_{j=1}^{i-1} a_j \qquad \text{Equation (1)}$$

When the effective area of the smallest subpixel is a, $a_1=a_2=\ldots=a_k=a$, $a_{k+1}=\alpha a$ (where α is a real number greater than 1), Equation (2) is obtained as $a_n$ satisfying Equation (1).

$$a_n = a(n \leq k), \, a_n = a\left(1 + \frac{\alpha}{k}\right)^{n-k-1} \alpha a \qquad \text{Equation (2)}$$

$$(k < n \leq N)$$

For a sum of $a_n$, a relation of Equation (3) is obtained.

$$\sum_{i=1}^{N} a_n = k\left(1 + \frac{\alpha}{k}\right)^{N-k} a \qquad \text{Equation (3)}$$

For example, when a is set to 0.05 mm in square and the sum of the effective areas of the subpixels is equal to the area of the pixel, α can be obtained for any k using Equation (3). Here, when the area of the pixel 20 is 1 mm in square and N=16 is set, α=0.49 is obtained for k=1 and α=0.92 is obtained for k=2. Thus, since α≤1 is satisfied for both cases, there is no solution. That is, the inventors have found that a desirable detector is not realized in some cases when the smallest subpixels are not formed by a number equal to or greater than a given value. Since α=1.37 is obtained for k=3, there is a solution. There is a solution for k=4 or more. However, the effective area of the largest subpixel is larger than in the case of k=3, and thus saturation occurs in a lower incident rate. Therefore, this is not desirable.

In practice, it is necessary to divide the pixel with a certain decided shape into subpixels. It is difficult to set a value close to 1 as the aspect ratio to reduce crosstalk or to divide the pixel into the subpixels precisely according to Equation (2) due to other restrictions. However, it is practical to divide the pixel into the subpixels with a difference of equal or less than 10% from a value given in Equation (2) and it is possible to obtain more effects intended in the invention.

FIG. 8 is a schematic diagram illustrating a ratio of a standard deviation of the counting from the incident rate in the radiation detector illustrated in FIG. 4 according to the embodiment. As the incident rate increases, a plurality of spots in which the standard deviation discontinuously increases can be seen. The spots are discontinuous points caused due to the saturation of the subpixels. By forming four or more subpixels and appropriately setting the areas of the subpixels, an increase in the standard deviation at the discontinuous points is suppressed and nearly constant behaviors can be realized in broad incident rate areas. By maintaining the total large area of the subpixels contributing to the acquisition of the data, the absolute value of the standard deviation is suppressed and the high precise counting is performed.

PTL 1 tells that a ratio of areas is in the range of about 1:4:8 to about 2:4:8 when the pixel is divided into four or more subpixels. It is considered that PTL 1 does not describe a case in which a plurality of smallest subpixels are formed and describes a case of k=1 mentioned in the embodiment. In the invention, however, $a_1:a_2:a_3=1:\alpha:\alpha(1+\alpha)=4/\alpha:4:4(1+\alpha)$. When $4/\alpha$ falls in the range of about 1 to 2, it is necessary for $\alpha$ to be about 2 to 4. However, in this case, $4(1+\alpha)$ is about 12 to 20, and thus considerably exceeds 8 disclosed in PTL 1. That is, the range disclosed in PTL 1 is different from that of the embodiment, and thus the idea disclosed in PTL 1 is understood to be different from that of the embodiment.

Strictly speaking, there is a possibility that the sum of the effective areas of the subpixels is not precisely identical to the geometric area of the pixel. The effective area of the subpixel is a value obtained by dividing a count rate of the subpixels by an incident rate and detection efficiency of the X-ray photons per unit area. As illustrated in FIG. 5, there is a gap which is a boundary of the subpixels between the subpixel electrodes 42. For example, a possibility that the X-ray photons incident on the gap is not correctly counted and a possibility that the X-ray photons incident on the vicinity of the side edges of the subpixels are not correctly counted due to a crosstalk effect are exemplified as factors. There is a possibility that the geometric areas of the subpixel electrodes are not precisely identical to the effective areas of the subpixels, but the effect is small and there is no influence on the gist of the embodiment.

Other Embodiments

The preferred embodiment has been described above, but various modifications and additions can be considered within the scope of the invention without departing from the gist of the invention.

For example, in the embodiment, the case in which the number of divided subpixels N=16 and the number of smallest subpixels k=3 are set has been described, but the numbers can be freely set according to the signal processing circuit, cost, or other circumstances as long as the numbers are in the range of N≥4 and 1≤k≤N−3. The method of taking the division regions of the subpixels can also be varied in various forms within the scope of the invention without departing from the gist of the embodiment.

In the embodiment, the detection of the X-ray photons has been described. However, the invention can also be applied to detectors for gamma-ray photons, ultraviolet-ray photons, and a charged particle beam. The application example to the whole-body CT has been described, but the invention can also be applied to a dental CT, a CT for an object other than a human object, an imaging device using an X ray including a homeland security orientation, and a nuclear medical diagnosis device such as SPECT or PET.

In the embodiment, the subpixels are divided by forming the common electrode on the upper surface of the direct radiation detection material and forming the subpixel electrodes on the lower surface of the direct radiation detection material. However, an electrode may be formed for each subpixel on the upper surface without forming the common electrode. Similarly, in the plurality of radiation detectors 150, the pixels 20 of the adjacent radiation detectors may share the common electrode on the upper surface or may include individual electrodes. A material in which photodevices are optically coupled in scintillator (indirect radiation detection material) can also be used as the material of the detector rather than the direct radiation detection material. As a method of dividing the subpixels, a scintillator of which a circumference is covered with a light-shielding agent may be formed for each subpixel or the pixel may be divided into subpixels in accordance with a technique of generating a microcrack between the subpixels in one scintillator by a laser. A photomultiplier tube (PMT), a photodiode (PD), an avalanche photodiode (APD), a silicon photomultiplier tube (SiPM), or the like can be used as the photodevice.

In the embodiment, a signal from each subpixel is processed by the individual channel 165 of the signal processing circuit, but a switch that can connect signals from the plurality of subpixels to the channels of one signal processing circuit may be formed. Thus, the plurality of subpixels can effectively be integrated to one large subpixel. Thus, in a region in which the incident rate is low, it is possible to suppress an influence of crosstalk. It is also possible to reduce the number of channels of the signal processing circuit to be used.

The radiation detectors according to the embodiment can be disposed in a plurality of layers in a direction parallel to an incident direction of a radiation ray. Thus, a radiation ray transmitted through the radiation detectors in an arrival direction of the radiation ray can be detected by the radiation detectors on the rear stage, and thus it is possible to improve detection efficiency.

REFERENCE SIGNS LIST 20 pixel
21 largest subpixel
22 smallest subpixel
23 subpixel
30 region in vicinity of center of pixel
40 direct radiation detection material
41 common electrode
42 subpixel electrode
50 centroid of pixel
51 centroid of subpixels contributing to acquisition of data when largest subpixel is saturated
52 movement trajectory of centroid of subpixels contributing to acquisition of data when subpixels with large effective areas are saturated in order
100 computer tomography device (CT)
110 gantry
120 X-ray source
130 X-ray photon
140 bed
150 plurality of radiation detectors
160 signal processing circuit
165 individual channel of signal processing circuit
170 control device
180 computer
190 interface
191 output device
192 input device
200 object

The invention claimed is:

1. A radiation detector comprising:
a plurality of flat pixels configured to detect a radiation ray,
wherein the pixel is divided into four or more subpixels of which at least two subpixels have different effective areas, and
wherein the pixel is divided into the subpixels so that even when an arbitrary number of subpixels less than the number of subpixels obtained by dividing the pixel is removed from the pixel in order of larger effective areas, a centroid of the effective area of the entirety of the remaining subpixels is positioned within a similar-shape region having the same centroid as the pixel and having sides of lengths that are half those of the pixel.

2. The radiation detector according to claim 1, wherein the subpixels have solid shapes.

3. The radiation detector according to claim 2, wherein the subpixels have square or rectangular shapes with an aspect ratio equal to or greater than 0.5 and equal to or less than 2.

4. The radiation detector according to claim 1, wherein in the pixel, the subpixel having a smallest effective area is formed at a position at which a side is not shared with the pixel.

5. The radiation detector according to claim 1, wherein the pixel is formed of a direct radiation detection material.

6. The radiation detector according to claim 1, wherein in the pixel, the plurality of subpixels with a smallest effective area are formed.

7. The radiation detector according to claim 1, wherein in the pixel, the subpixels having a same effective area are disposed distant from each other inside the pixel.

8. The radiation detector according to claim 1, wherein when the effective areas of the subpixels are $a_1, a_2, \ldots,$ and $a_N$ (where N is a natural number equal to or greater than 4) in order of the smaller effective areas, the effective areas of the subpixels are set such that sizes of the effective areas of the subpixels are substantially identical to a value given by an equation below:

$$a_n = a(n \leq k), \ a_n = a\left(1 + \frac{\alpha}{k}\right)^{n-k-1} a$$

$$(k < n \leq N),$$

where a is an effective area of a smallest subpixel and k is a natural number equal to or greater than 1 and equal to or less than N−3, and α is a real number greater than 1.

9. The radiation detector according to claim 1, wherein the subpixels operate in a pulse mode.

10. A radiation imaging device comprising:
the radiation detector according to claim 1, in which a signal processing channel is connected to the subpixel,
wherein a signal for forming an image is output from the signal processing channel.

11. A computer tomography device (CT) comprising:
the radiation detector according to claim 1.

12. A radiation detection method causing a computer processing radiation detection data detected by the radiation detector according to claim 1 to perform:
acquiring the radiation detection data detected with subpixels other than saturated subpixels in a case in which some of the subpixels included in a pixel are saturated; and
correcting the acquired radiation detection data depending on the subpixels from which the radiation detection data is acquired.

* * * * *